(12) United States Patent
Amirouche et al.

(10) Patent No.: US 8,197,549 B2
(45) Date of Patent: Jun. 12, 2012

(54) SYSTEM AND METHOD FOR PROSTHETIC FITTING AND BALANCING IN JOINTS

(75) Inventors: Farid Amirouche, Highland Park, IL (US); Mark H. Gonzalez, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 207 days.

(21) Appl. No.: 12/539,283

(22) Filed: Aug. 11, 2009

(65) Prior Publication Data

US 2009/0299483 A1 Dec. 3, 2009

Related U.S. Application Data

(62) Division of application No. 10/393,243, filed on Mar. 19, 2003, now Pat. No. 7,575,602.

(60) Provisional application No. 60/365,678, filed on Mar. 19, 2002.

(51) Int. Cl.
*A61F 2/38* (2006.01)
*A61B 5/103* (2006.01)

(52) U.S. Cl. ..................... 623/20.29; 600/587

(58) Field of Classification Search ............... 623/20.29, 623/18.11, 20.14, 20.32, 20.31, 23.47, 908, 623/914, 38; 606/102, 86 R, 87, 88; 600/587, 600/595; 73/172, 862.46, 862; 128/898
See application file for complete search history.

(56) References Cited

U.S. PATENT DOCUMENTS 5,197,488 A * 3/1993 Kovacevic ................ 600/595

(Continued)

FOREIGN PATENT DOCUMENTS

DE 197 09 60 A1 9/1998

(Continued)

OTHER PUBLICATIONS

Amirouche, F., Aram, L., Gonzalez, M., Giachetti, R., Mahr, C., "The Fitting of the Human Joint Through Micro Implanted Sensors", Proceedings of the 1st Annual International IEEE—EMBS Special Topic Conference on Microtechnologies in Medicine & Biology, Oct. 2000.

(Continued)

*Primary Examiner* — Pedro Philogene
(74) *Attorney, Agent, or Firm* — Marshall, Gerstein & Borun LLP

(57) ABSTRACT

A system and method for prosthesis fitting in joints comprising an artificial condyle and a spacer which cooperates with the condyle to form an artificial joint. The spacer embedded with at least one sensor which is responsive to a force generated between the condyle and the spacer. The artificial joint is adapted to move between a flexed position and an extended position defining a range of motion. The sensor is responsive to the force and generates an output representative of that force. The output is transmitted, either wirelessly or other, to a processor which utilizes an analysis program to display a representation of the forces applied. A practitioner utilizing the displayed analysis may intraoperatively determine the adjustments and balancing required within the artificial joint. The system may also utilize a ligament tension sensor which generates generates data representative of tension on a ligament of the artificial joint, and a joint angle sensor responsive to the range of motion of the artificial joint. The processor may be adapted to store the outputted sensor data to provide the practitioner with statistically relevant historical data.

47 Claims, 16 Drawing Sheets

U.S. PATENT DOCUMENTS

| | | | | |
|---|---|---|---|---|
| 5,289,826 | A * | 3/1994 | Kovacevic | 600/587 |
| 5,360,016 | A * | 11/1994 | Kovacevic | 600/595 |
| 5,470,354 | A * | 11/1995 | Hershberger et al. | 128/898 |
| 5,533,519 | A * | 7/1996 | Radke et al. | 600/595 |
| 5,656,785 | A * | 8/1997 | Trainor et al. | 73/862.46 |
| 5,733,292 | A * | 3/1998 | Gustilo et al. | 606/88 |
| 5,880,976 | A | 3/1999 | DiGioia III et al. | |
| 6,447,448 | B1 * | 9/2002 | Ishikawa et al. | 600/300 |
| 7,537,573 | B2 * | 5/2009 | Horst | 601/5 |
| 7,575,602 | B2 * | 8/2009 | Amirouche et al. | 623/18.11 |

FOREIGN PATENT DOCUMENTS

| | | |
|---|---|---|
| DE | 200 16 635 U2 | 3/2001 |
| EP | 0 979 636 A2 | 2/2000 |
| WO | WO-92/17113 | 10/1992 |
| WO | WO-97/30652 | 8/1997 |
| WO | WO-99/35972 | 7/1999 |
| WO | WO-01/15058 A1 | 3/2001 |

OTHER PUBLICATIONS

Amirouche, F., Giachetti, R., Aram, L., Gonzalez, M., "Induced Stress in TKA Resulting from Malrotation," Proceedings of the ASME Bioengineering Conference, Jun. 2001.

Amirouche, F., Giachetti, R., Aram, L., Gonzalez, M., "Validation of a Finite Element Contact Model for the Use in Total Knee Arthroplasty", Proceedings of XVIIIth Congress of the International Society of Biomechanics, Jul. 2001.

Amirouche, F.M.L., Gonzales, M. et al., "Geometrical Analysis of Potential Error in using Femoral Intramedullary Guides in Total Knee Arthoplasty," Journal of Arthoplasty.98.227. to appear Dec. 2000.

Aram, L., Amirouche, F., Gonzalez, M., Giachetti, R., "Characterization of Contact Pressure in Total Knee Arthroplasaty as a Function of Component Position and Ligament Balance," Proceedings of the International Society of Biomechanics, Jul. 2001.

Beard, B.J., Natarajan, R.N., Andriacchi, T.P., Amirouche, F.M.L, "The Stress Origins of a New Striated Wear Pattern in a Total Knee Replacements", Transactions of 42nd Annual Meeting of Orthopedic Research Society, pp. 465. 1996.

Chandran, N., Amirouche, F.M.L., "Effect of Malalignment and Friction on Contact Pressure in the Polyehtylene Compent of the TKR ASME" Bioengineering Division, 2002.

Chandran, N., Amirouche, F.M.L., "Effect of Slope Changes in Posterior Stabilizer on the Rollback Mechanism of the Knee in Flexion-Extension ASME," Bioengineering Summer Conference 2003.

Giachetti, R., Amirouche, F., Aram, L., Gonzalez, M., "Biomechanical Problems with Contact Pressure Distribution in the Knee Joint after Total Knee Arthroplasty," Proceedings of the ASME Winter Conference, Nov. 2000.

Natarajan, R.N., Andriacchi, T.P. Beard, B.J., Amirouche, F.M.L, "Fatigue Failure Prediction in the Polyethylene Component of a Total Knee Replacement Based on Cyclic Rolling", BED-vol. 33, Bioengineering Conference, ASME, pp. 421-422, 1996.

Varadarajan, R., Amirouche, F.M.L., Wagner, F., Guppy, K., "A Finite Element Study of Osteoporosis in a Disc Degenerated Lumbar Spine Subject to Axial Compression", ASME—Bioengineering Division, 2002.

* cited by examiner

SYSTEM AND METHOD FOR PROSTHETIC FITTING AND BALANCING IN JOINTS

CROSS-REFERENCE TO RELATED APPLICATION

This application is a divisional of application Ser. No. 10/393,243 filed Mar. 19, 2003, which claims the benefit of priority from U.S. provisional patent application No. 60/365,678, filed Mar. 19, 2002.

FIELD OF THE INVENTION

The present invention relates to joint replacement and, more particularly, to a system and method for prosthesis fitting and balancing in joints.

BACKGROUND OF THE INVENTION

Some medical conditions can result in the degeneration of a human joint, causing a patient to consider and ultimately undergo joint replacement surgery. While joint replacement surgery is well known in the art, the decision to undergo such a procedure may be a difficult one, as the long-term success of the surgery oftentimes relies upon the skill of the surgeon and may involve a long, difficult recovery process.

The materials used in a joint replacement surgery are designed to enable the joint to move just like a normal joint. The prosthesis is generally composed of a metal piece that fits closely into and bears on a corresponding plastic component. The plastic component is typically supported on another metal piece. Several metals are typically used, including stainless steel, alloys of cobalt and chrome, and titanium, while the plastic material is typically constructed of a durable and wear resistant polyethylene. Plastic bone cement may be used to anchor the prosthesis into the bone, however, the prosthesis may be implanted without cement when the prosthesis and the bone are designed to fit and lock together directly.

To undergo the operation, the patient is given an anesthetic while the surgeon replaces the damaged parts of the joint. For example, in knee replacement surgery, the damaged ends of the bones (i.e., the femur and the tibia) and the cartilage are replaced with metal and plastic surfaces that are shaped to restore knee movement and function. In another example, to replace a hip joint, the damaged ball (the upper end of the femur) is replaced by a metal ball attached to a metal stem fitted into the femur, and a plastic socket is implanted into the pelvis, replacing the damaged socket. Although hip and knee replacements are the most common, joint replacement can be performed on other joints, including the ankle, foot, shoulder, elbow and fingers.

As with all major surgical procedures, complications can occur. Some of the most common complications are typically thrombophlebitis, infection, stiffness, and loosening. While thrombophlebitis (i.e., vein inflammation related to a blood clot) and infection are oftentimes treated medically, stiffness and loosening may require additional surgeries. One technique utilized to reduce the likelihood of stiffness and loosening relies upon the skill of the surgeon to align and balance the replacement joint along with ligaments and soft tissue during surgery.

DETAILED DESCRIPTION OF THE PREFERRED EMBODIMENT

Figure 1:
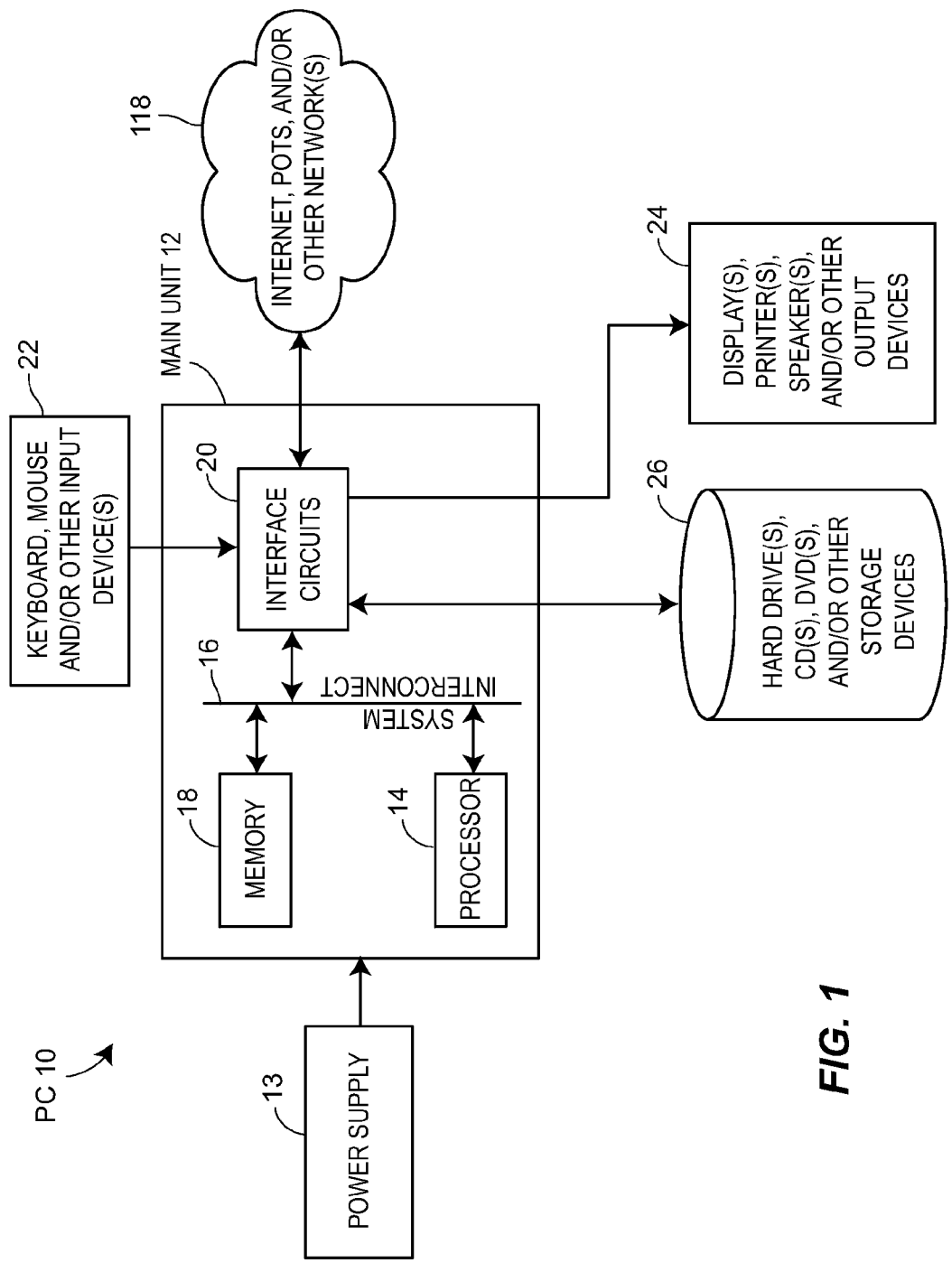
FIG. 1 is a block diagram of a computer system illustrating an example environment of use for the disclosed system.

A block diagram of an example computer system 10 is illustrated in FIG. 1. The computer system 10 may be a personal computer (PC) or any other computing device capable of executing a software program. In an example, the computer system 10 includes a main processing unit 12 powered by a power supply 13. The main processing unit 12 illustrated in FIG. 1 includes one or more processors 14 electrically coupled by a system interconnect 16 to one or more memory device(s) 18 and one or more interface circuits 20. In an example, the system interconnect 16 is an address/data bus. Of course, a person of ordinary skill in the art will readily appreciate that interconnects other than busses may be used to connect the processor(s) 14 to the memory device(s) 18. For example, one or more dedicated lines and/or a crossbar may be used to connect the processor(s) 14 to the memory device(s) 18.

The processor(s) 14 may include any type of well known microprocessor, such as a microprocessor from the Intel Pentium™ family of microprocessors. The illustrated main memory device 18 includes random access memory such as, for example, dynamic random access memory (DRAM), or static random access memory (SRAM), but may also include non-volatile memory. In an example, the memory device(s) 18 store a software program which is executed by one or more of the processors(s) 14 in a well known manner.

The interface circuit(s) 20 are implemented using any type of well known interface standard, such as an Ethernet interface and/or a Universal Serial Bus (USB) interface. In the illustrated example, one or more input devices 22 are connected to the interface circuits 20 for entering data and commands into the main processing unit 12. For example, an input device 22 may be a keyboard, mouse, touch screen, track pad, track ball, isopoint, and/or a voice recognition system.

Figure 17:
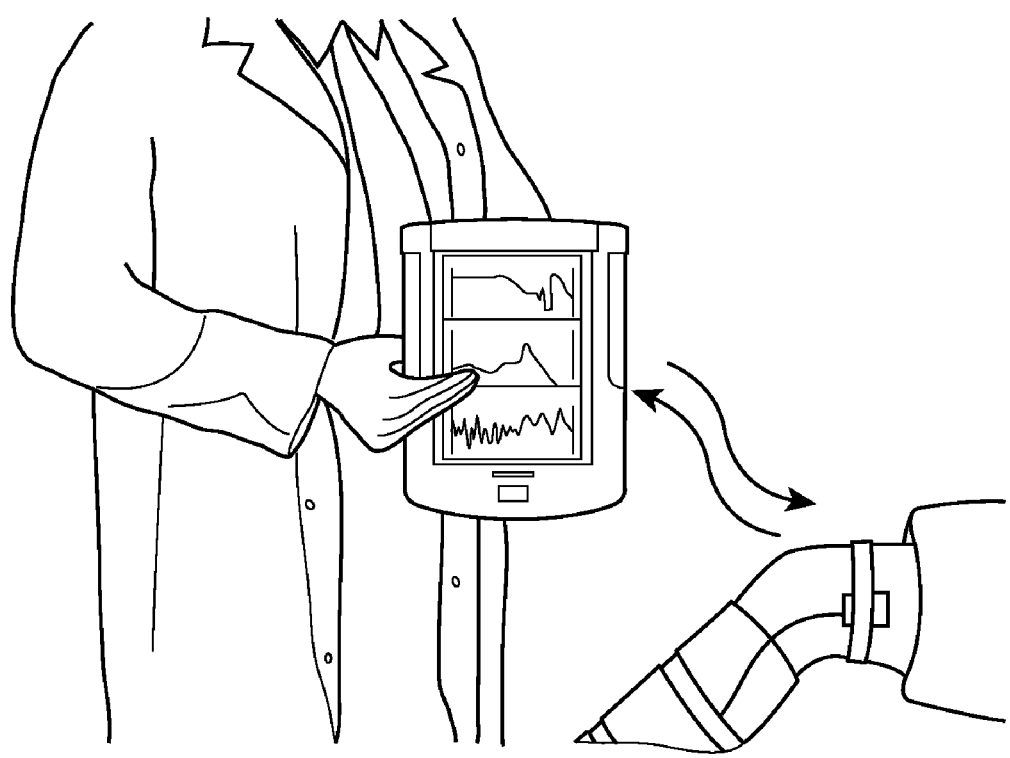
FIG. 17 is a diagrammatic view of a wireless graphical hand-held output display in accordance with one possible form of the present invention.

In the illustrated example, one or more displays, printers, speakers, and/or other output devices 24 are also connected to the main processing unit 12 via one or more of the interface circuits 20. The display 24 may be a cathode ray tube (CRT), a liquid crystal display (LCD), or any other type of display, such as a hand-held display 500 as shown in FIG. 17. The display 24 may generate visual indications of data generated during operation of the main processing unit 12. For example, the visual indications may include prompts for human operator input, calculated values, detected data, etc.

The illustrated computer system 10 also includes one or more storage devices 26. For example, the computer system 10 may include one or more hard drives, a compact disk (CD) drive, a digital versatile disk drive (DVD), and/or other computer media input/output (I/O) devices.

The illustrated computer system 10 may also exchange data with other devices via a connection to a network 118. The network connection may be any type of network connection, such as an Ethernet connection, digital subscriber line (DSL), telephone line, coaxial cable, etc. The network 118 may be any type of network, such as the Internet, a telephone network, a cable network, and/or a wireless network.

Figure 2:
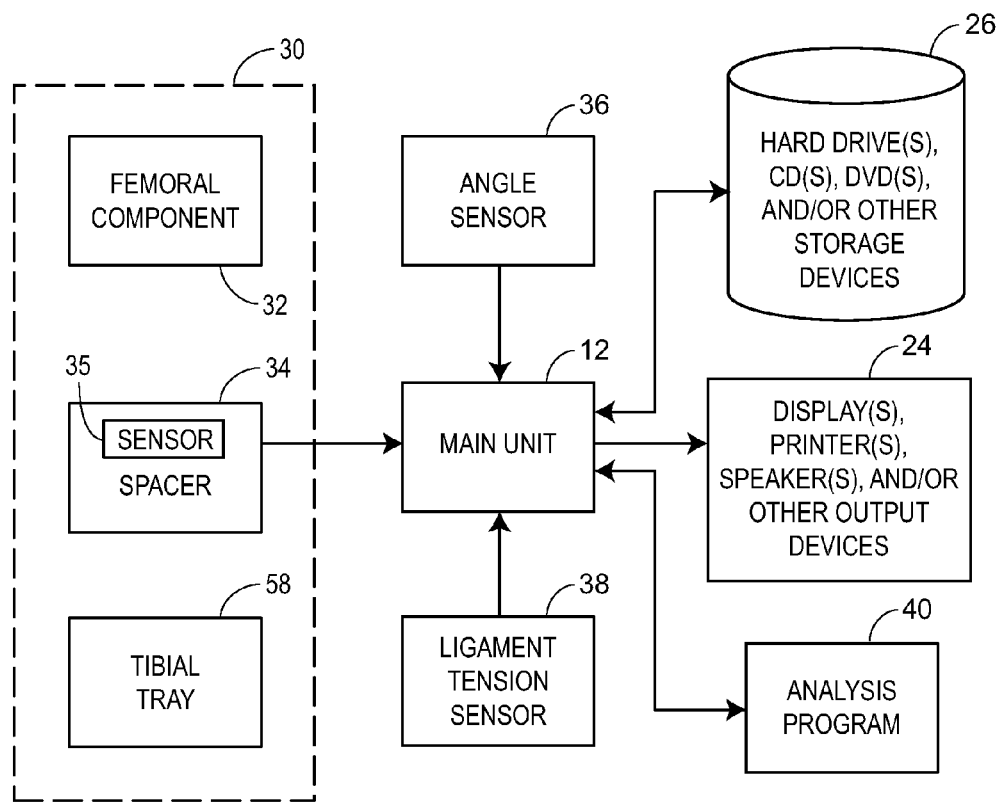
FIG. 2 is a block diagram of a joint prosthesis fitting and balancing system.

An example system for prosthesis fitting and balancing in joints is illustrated in FIG. 2. In one embodiment, the system includes a prosthesis 30, a joint angle sensor 36, a ligament tension sensor 38, an analysis program 40, the main unit 12, the one or more storage devices 26, and the display 24. As will be described in detail below, the artificial joint may comprise a femoral component 32, a tibial tray 58, and a spacer 34 with one or more imbedded sensors 35. Any or all of the sensors 35, 36, 38 may be implemented by conventional sensor technology, including commercially available pressure sensors, tension sensors, and angle sensors. Furthermore, any or all of the storage device 26, and the analysis program 40 may be implemented by conventional electronic circuitry, firmware, and/or by a microprocessor executing software instructions in a well known manner. However, in the illustrated example, the analysis program 40 is implemented by software stored on the memory 18 and executed by the processor 14, while the storage device 26 may be implemented by database server software stored on the memory 18, and executed by the processor 14 to physically store data on a hard drive. In addition, a person of ordinary skill in the art will readily appreciate that certain modules in the apparatus shown in FIG. 2 may be combined or divided according to customary design constraints. Still further, one or more of the modules may be located external to the main processing unit 12.

Figure 3:
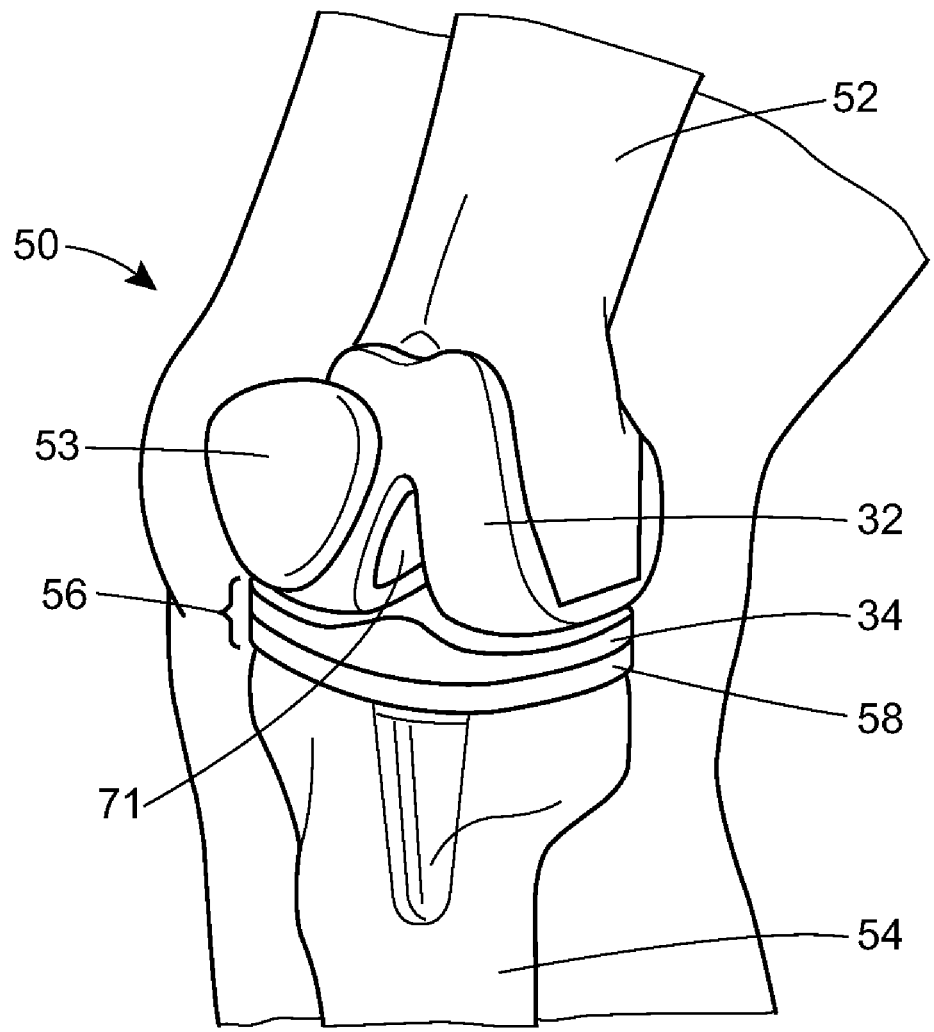
FIG. 3 is a front perspective view of an embodiment of a prosthesis fitted within a human knee.

Turning to FIG. 3, there is shown an example of the prosthesis 30 as used in conjunction with the replacement of a human knee 50. In general, the human knee 50 comprises a femur 52, a patella 53, a tibia 54, a plurality of ligaments (not shown), and a plurality of muscles (not shown). The prosthesis 30 generally comprises two parts, the femoral component 32 and a tibial component 56. Additionally, the tibial component 56 is typically made up of two parts, the metal tibial tray 58 that is attached directly to the tibia 54 and the spacer 34 that provides the bearing surface. It will be understood that the while in the disclosed embodiment the tibial component 56 is comprised of separate components, the spacer 34 and the metal tibial tray 58 may be integrally formed. The materials used in a joint replacement surgery are designed to enable the joint to mimic the behavior or a normal knee joint.

In the illustrated embodiment, the femoral component 32 is a metal piece, shaped similar to the end of the femur and fitting closely into a corresponding plastic spacer 34. Several metals are typically used, including stainless steel, alloys of cobalt and chrome, and titanium, while the plastic material is typically constructed of a durable and wear resistant polyethylene. Other suitable materials may now exist or may be developed in the future. Plastic bone cement may be used to anchor the prosthesis 30 into the bones 52, 54, however, the prosthesis 30 may be implanted without cement when the prosthesis 30 and the bones 52, 54 are designed to fit and lock together directly. A cemented prosthesis 30 is held in place by a type of epoxy cement that attaches the metal to the bones 52, 54. An uncemented prosthesis 30 has a fine mesh of holes on the surface that allows the bones 52, 54 to grow into the mesh and attach the prosthesis 30 to the bones 52, 54.

Figure 4:
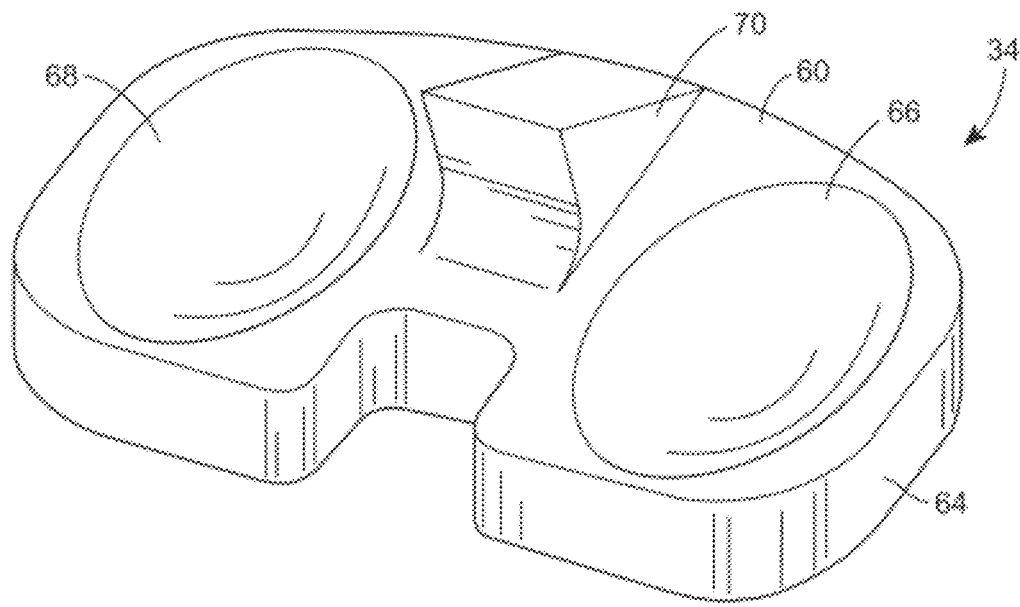
FIG. 4 is a top perspective view of an embodiment of a spacer of the system of FIG. 2.
Figure 5:
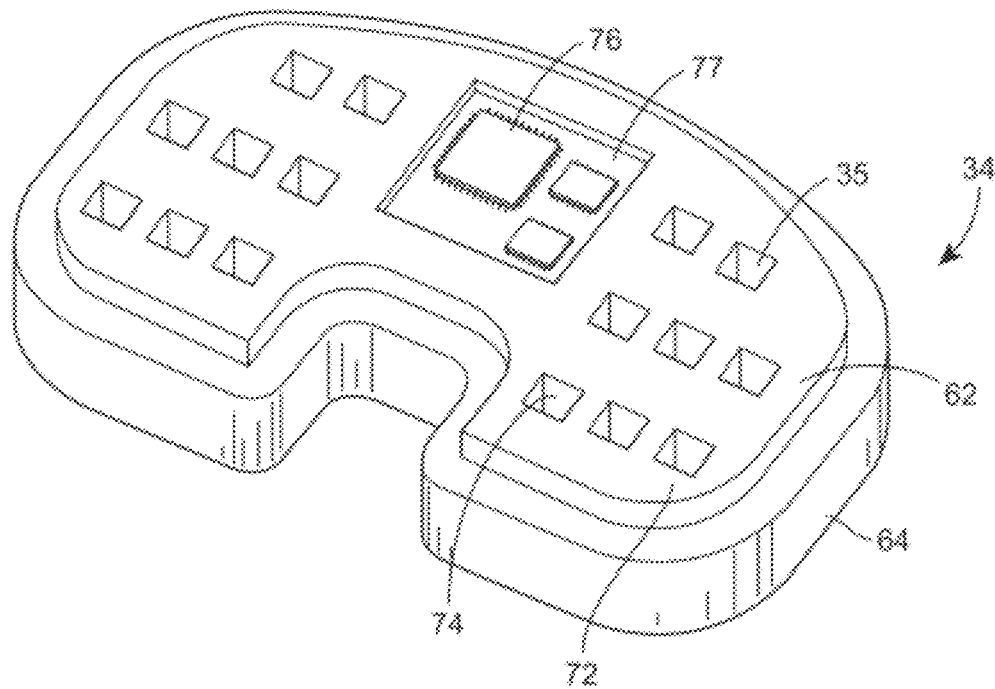
FIG. 5 is a bottom perspective view of the spacer of FIG. 4.

Referring now to FIGS. 4 and 5, there is illustrated an example spacer 34 which may be used in conjunction with an embodiment of the system of FIG. 2. The spacer 34 includes a pair of opposed faces 60, 62 and an elongated side edge 64. The face 60 comprises a pair of condyle recesses 68, 66, shaped to closely match or otherwise accommodate the shaped end of the femoral component 32. The face 60 may also comprise an extension 70 which may slidably engage a groove 71 in the femoral component 32 and prevent lateral movement between the spacer 34 and the femoral component 32, while allowing the two pieces to rotate relative to each other in a predefined range of motion similar to a biological knee, for example, between zero degrees (0°), i.e., extension, and ninety degrees (90°), i.e., flexion. The contact between the femoral component 32 and the spacer 34 will produce deformations in the two surfaces in contact, which may be measured by the sensors 35 embedded in the spacer 34. The sensed deformation may cause an output to be created by the sensors 35.

The opposite face 62 includes an elevated face 72. The elevated face 72 and the face 62 cooperate to form a snap-fit connection with the tibial tray 58 as is well known in the art. It will be noted that connection between the tibial tray 58 and the spacer 34 may vary according to known design variations. For instance, the elevated face 72 and the face 62 may be substantially coplanar and may be cemented onto the tibial tray 58.

In the illustrated embodiment of FIG. 5, the elevated face 72 is illustrated with a plurality of recesses 74. The recesses 74 are milled in the face 72 of the polyethylene and have a cross section sized to accept sensors 35, thereby enabling the sensors 35 embedded in the spacer 34. Since the sensors 35 are responsive to the deformation of the spacer 34, the depth of the recesses 74 may be chosen to minimize the impact on the deformation characteristics of the spacer 34, as well as to ensure an accurate reading based on the sensitivity of the sensor 35.

For example, in the illustrated embodiment, the recesses 74 have a cross section of appropriately dimensioned to accept a strain sensor marketed by Omega Engineering, Inc., of Stanford, Conn. In one embodiment, the recesses are arranged in an array and include a bar-shaped micro miniature strain gage (sensor 35) of approximate dimension 1 mm×0.5 mm×0.15 mm. The strain gage is responsive to the deformation of curvature with a maximum strain of 3000μ. Furthermore, the strain gage may provide data in a real-time, or near real-time fashion, allowing for intraoperative analysis of the data. A person of ordinary skill in the art will readily appreciate that other sensors may be used to sense the deformation of the spacer 34. For example, a single sensor, or an array of sensors may be used to sense the deformation of the spacer 34.

Once the sensor 35 is placed in the recesses 74, the recesses may be filled with a plug of the same, or similar, material as the spacer 34, to further minimize the impact on the deformation characteristics of the spacer 34. The recess plug may be, for example, glued in place, or held by an interference fit. Of course, a person of ordinary skill in the art will readily appreciate that any number of recesses 74 and sensors 35 may be utilized. Moreover, the dimensions of the recesses may vary greatly, depending upon the characteristics of the spacer 34, the sensor 35, and/or the desired sensitivity. Still further, it will be appreciated that the sensors 35 may be embedded within the spacer 34 utilizing any known or yet to be developed manufacturing method, including direct insertion during the molding process, as well as insertion utilizing a transverse cut in the spacer 34.

The spacer 34 illustrated in FIG. 5 includes a plurality of sensors 35 electrically coupled by a system interconnect (not shown) to one or more transceiver device(s) 76. In the example, the system interconnect is a plurality of wires (not shown) transversely carried through the spacer 34 to the transceiver device(s) 76. Of course, a person of ordinary skill in the art will readily appreciate that interconnects other than wires may be used to connect the sensors 35 to the transceiver devices(s) 76. For example, one or more wireless connections may be used to connect the sensors 35 to the transceiver device(s) 76. In the illustrated embodiment, the transceiver device(s) 76 is embedded within another recess 77 within the elevated face 72 of the spacer 34, however, it will be understood that the transceiver may be located in any location, including external to the spacer 34.

In one embodiment, the transceiver device(s) 76 is a self powered, 5 channel input transceiver having approximate dimensions of 1.46 cm×3.05 cm×0.65 cm. The transceiver has a sample rate of 150 samples per second and is powered by a 3.1 volt minimum, 7 volt maximum, 13.8 DC battery. Additionally, the transceiver may contain a memory for storing sensor data. In operation, the transceiver device 76 is adapted to receive, as an input, multiple sensor outputs created by each of the sensors 35 in response to the deformation of the spacer 34. The transceiver device 76 is further adapted to convert the multiple sensor inputs to a serial data stream and transmit the data stream, via wired or wireless connection, to the main unit 12. The transceiver devices 76 is preferably a single battery powered transceiver capable of wireless transmission, however, it may be any type of transceiver known or yet to be developed, such as a magnetically powered transceiver. Furthermore, it will be appreciated by one of ordinary skill in the art that the transceiver device(s) 76 and the sensors 35 may be combined or divided according to customary design constraints. Still further, the spacer 34 with embedded sensors 35 may be designed to be substantially permanently attached to the tibial tray 58, i.e., bioengineered to remain in the prosthesis 30 after surgery, or it may be temporarily attached to the tibial tray 58, i.e., to be used only during the actual replacement surgery to gather data and replaced by a substantially permanent spacer. In the disclosed example, this is aided by the fact that the sensors 35, etc. are fully encapsulated in the spacer 34.

Figure 7:
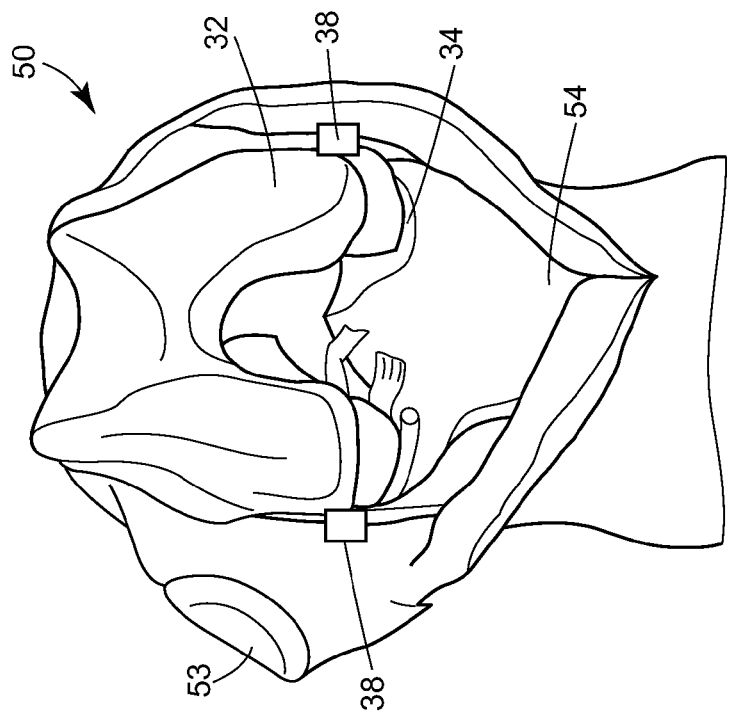
FIG. 7 is a front perspective view of an embodiment of a portion of the system of FIG. 2.
Figure 6:
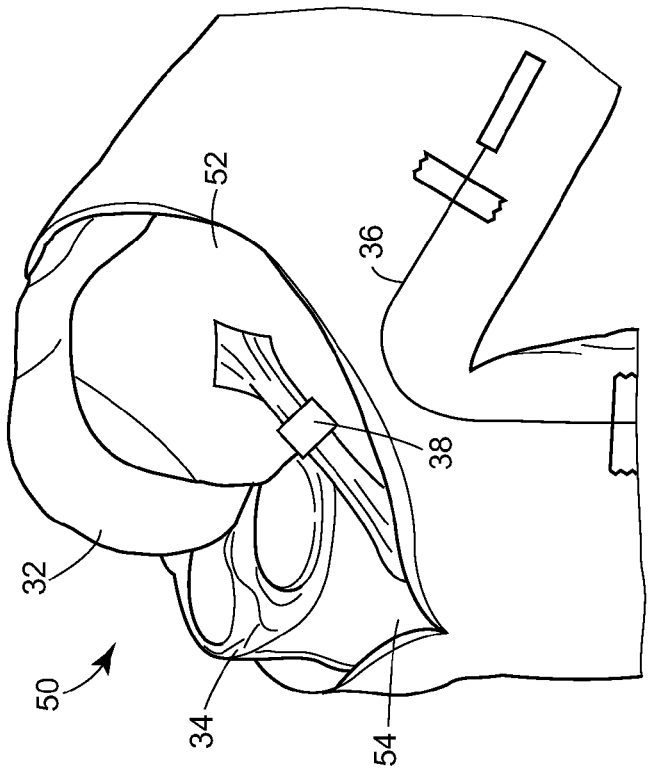
FIG. 6 is a side perspective view of an embodiment of a portion of the system of FIG. 2.

Referring now to FIGS. 6 and 7, there is illustrated a human knee exposed for surgery with the prosthesis 30 and sensors 35, 36, 38 in place. Specifically, the femoral component 32 is attached to the femur 52, and the tibial component 56 is attached to the tibia 54. The spacer 34 and embedded sensors 35 are in place between the femoral component 32 and the tibial tray 58. In the illustrated embodiment, a plurality of ligament tension sensors 38 are attached to external knee ligaments, such as, for example, the medial cruciate ligament and the lateral cruciate ligament. Additionally, the joint angle sensor 36 may be attached to the surface of the human knee 50.

The ligament tension sensors 38 may be any commercially available tension sensors such as one marketed by Omega Engineering, Inc., of Stanford, Conn. The ligament tension sensor 38 is responsive to the tension of the ligament to which it is attached, and is adapted to produce an output in response to the sensed tension. The ligament tension sensor 38 may also comprise a transceiver (not shown) similar to the above-described transceiver device 76. The data output from the ligament tension sensor 38 may thereby be transmitted to the main unit 12.

The joint angle sensor 36 may be any commercially available angle sensor such as—one marketed by Omega Engineering, Inc., of Stanford, Conn. The joint angle sensor 36 is responsive to the range of motion of the prosthesis 30, and is adapted to produce an output representative of the joint angle. The joint angle sensor 36 may also comprise a transceiver (not shown) similar to the above-described transceiver device 76. The data output from the joint angle sensor 36 may thereby be transmitted to the main unit 12.

As will be appreciate by one of ordinary skill in the art, the sensors 35, 36, 38 may be used in any number of combinations, depending upon the desired data collection strategy. For example, a practitioner may only be interested in the pressure between the spacer 34 and the femoral component 32 when the prosthesis is fully extended, and may therefore, only utilize the sensor 35 and the joint angle sensor 36.

Once all the desired sensors 35, 36, 38 are in place, it may be desirable to partially close the incision to evaluate the prosthesis 30 range of motion during flexion and extension. The surgeon may then flex the prosthesis 30 through its normal range of motion. The outputs from the sensors 35, 36, 38 are transmitted to the main unit 12, wherein they may be captured by the analysis program 40. In one embodiment, the analysis program 40 may be, for example, LabVIEW™ data acquisition software marketed by National Instruments Corp., of Austin, Tex. and commercially available.

The analysis program 40 may display the data in a variety of formats on the display(s) 24, as will be described below. The analysis program 40 may be adapted to transmit the acquired data to the database server software stored on the memory 18, and executed by the processor 14 to physically store data on a hard drive.

In one embodiment, as shown by FIGS. 8 through 10A, the sensor 35, 38 measurements are captured by the analysis program 40 and displayed as a pressure distribution graph. Specifically, referring to FIGS. 8 and 8A, the analysis program 40 displays a three dimensional pressure distribution graph 100, in pounds per square in (lb/in$^2$) when the prosthesis 30 is in the zero degree (0°) extension position (illustrated by FIG. 8). As described in detail above, the pressure distribution graph is representative of the sensed pressure on the spacer 34 by the femoral component 32. The illustrative pressure distribution graph 100 displays six regions of pressure sensor readings, namely an anterior 102, 104, a middle 106, 108, and a posterior region 110, 112, duplicated on both the medial and lateral portions of the spacer 32 respectively. It will be understood that while six regions 102, 104, 106, 108, 110, 112 are displayed, each region may be comprised of any number of individual sensor readings, including multiple readings per region.

Figure 10:
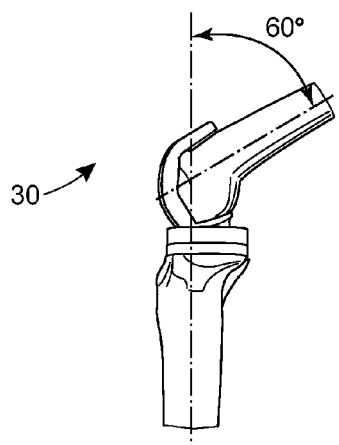
FIG. 10 is a side view of an embodiment of a prosthesis fitted within a human knee, wherein the knee is bent at sixty degrees.
Figure 10A:
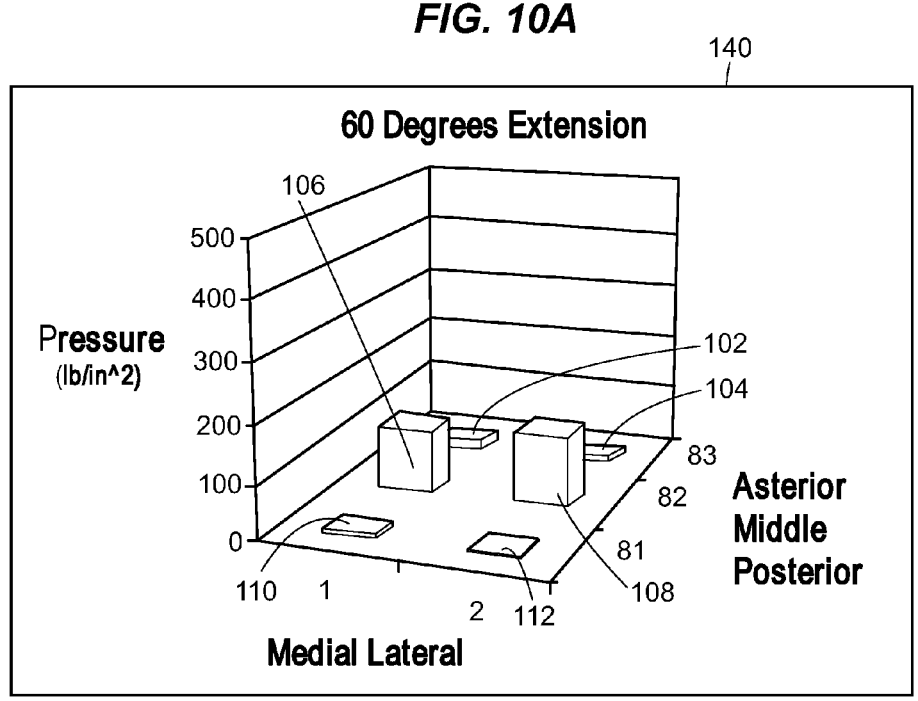
FIG. 10A is a graph plotting pressure readings in the prosthesis of FIG. 10.

Referring to FIGS. 9 and 9A, and FIGS. 10 and 10A, the analysis program 40 displays a three dimensional pressure distribution graph 120, 140 in pounds per square in (lb/in$^2$) when the prosthesis 30 is in the thirty degree (30°) extension position (illustrated by FIG. 9), and when the prosthesis 30 is in the sixty degree (60°) extension position (illustrated by FIG. 10). As described in above, the illustrative pressure distribution graphs 120, 140 display six regions of pressure sensor readings, namely an anterior 102, 104, a middle 106, 108, and a posterior region 110, 112, duplicated on both the medial and lateral portions of the spacer 32 respectively.

Figure 8:
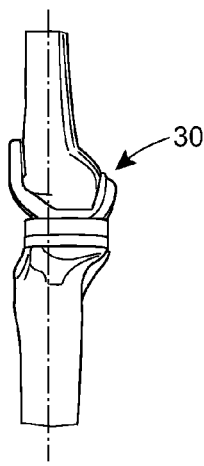
FIG. 8 is a side view of an embodiment of a prosthesis fitted within a human knee, wherein the knee is bent at zero degrees.
Figure 8A:
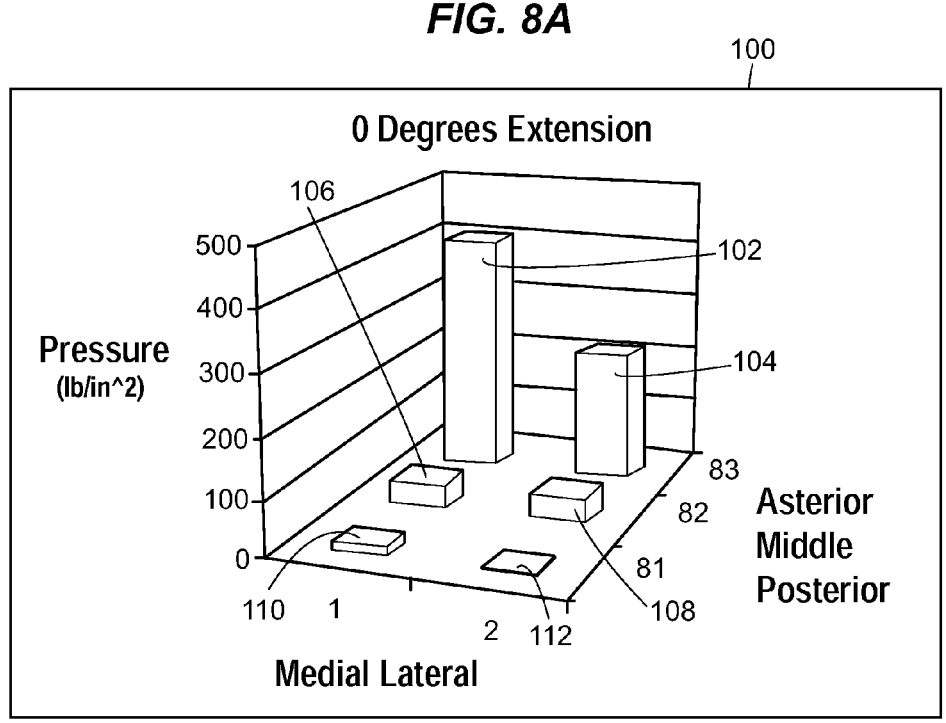
FIG. 8A is a graph plotting pressure readings in the prosthesis of FIG. 8.
Figure 9:
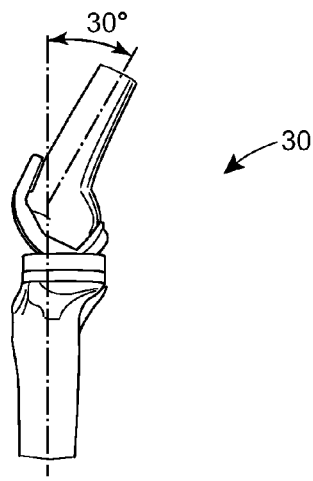
FIG. 9 is a side view of an embodiment of a prosthesis fitted within a human knee, wherein the knee is bent at thirty degrees.
Figure 9A:
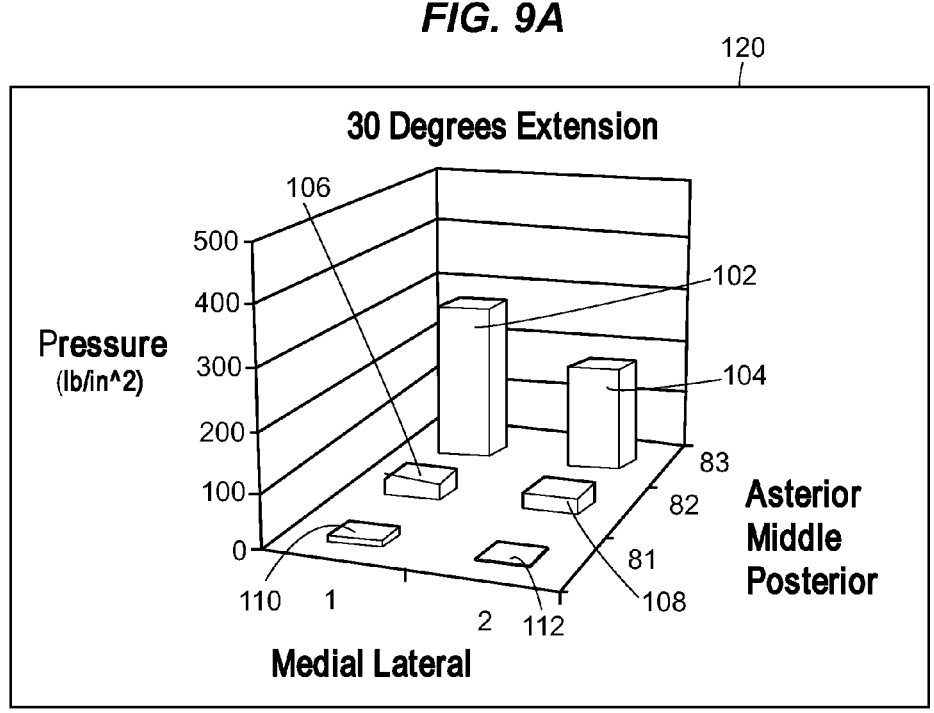
FIG. 9A is a graph plotting pressure readings in the prosthesis of FIG. 9.

The graphical pressure distribution graphs may allow the physician to adjust their surgical or medical procedures by examining the pressure within the prosthesis 30 at certain angles. For example, the physician may recognize, either by experience or knowledge of design constraints, that the medial anterior pressure region 102 of FIG. 8A is slightly elevated and may adjust the prosthesis 30 accordingly. Additionally, the analysis program 40 may provide the physician with the tension readings provided by the ligament tension sensors 38 (not shown) to aid the physician in determining whether, based upon the knowledge and skill of the surgeon, the ligaments should be adjusted.

In yet another embodiment, the analysis program 40 may be adapted to compare the acquired data to the data stored by the database server software on the hard drive. For example, upon the collection of a number of trials of empirical data, the stored data may be statistically analyzed (either by the analysis program 40, or another external program) to form suggested pre-determined pressure criteria, i.e., upper and lower limits, to aid the physician in recognizing potential elevated pressure readings. The suggested pre-determined pressure criteria may define statistically sound thresholds and allowable limits under certain conditions, and may be constantly adjusted as more information becomes available in the database.

Figure 11:
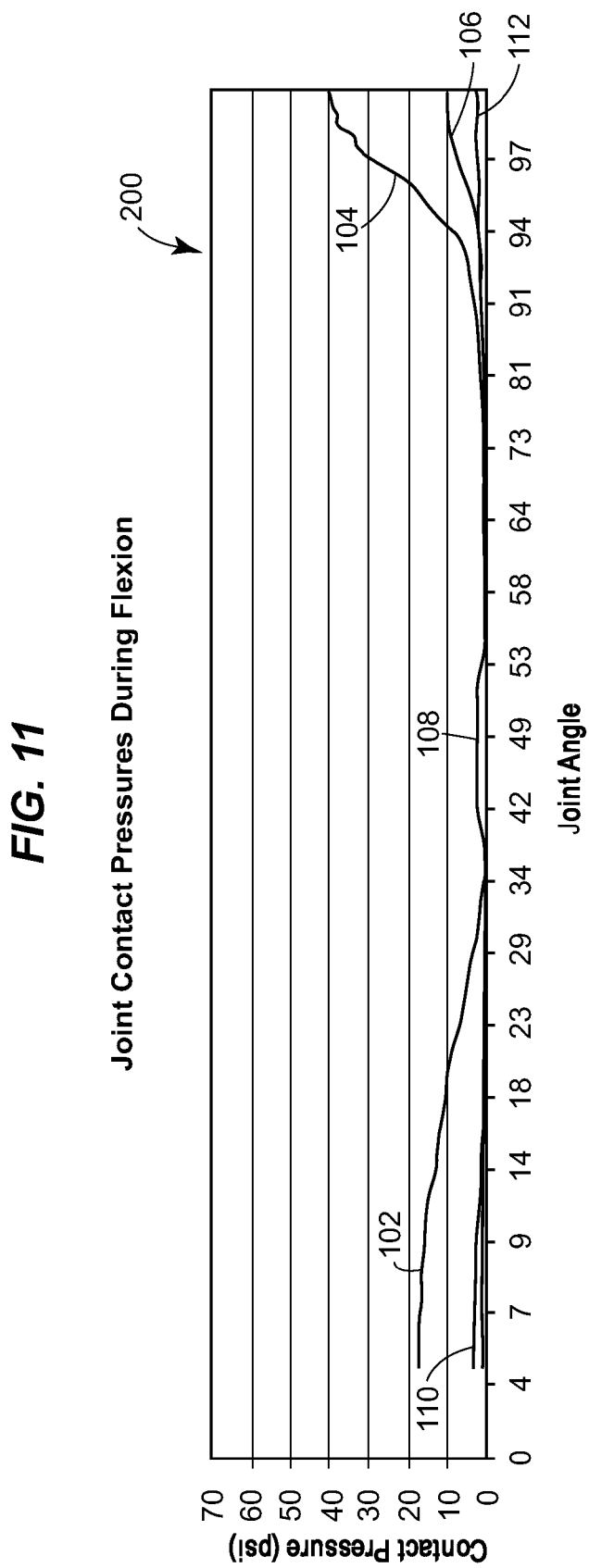
FIG. 11 is a graph plotting pressure readings as a function of joint angle of a prosthesis of FIG. 2 during flexion of the prosthesis.
Figure 12:
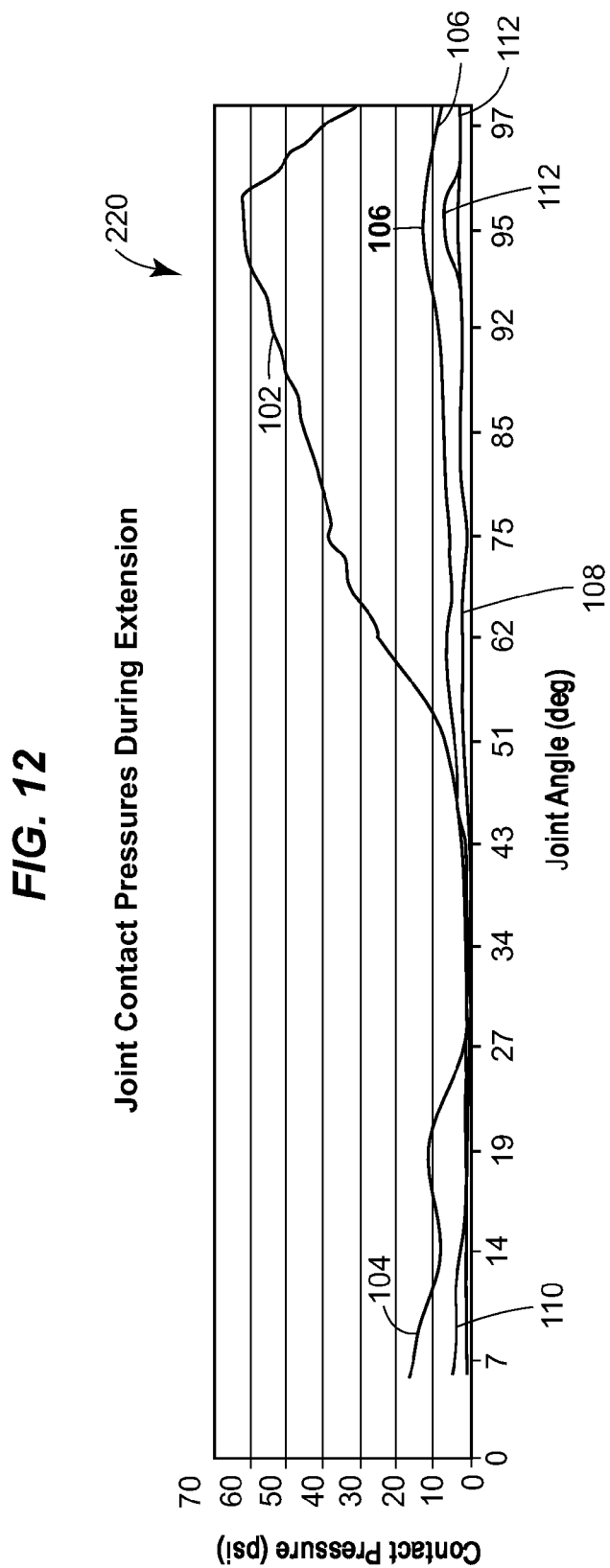
FIG. 12 is a graph plotting pressure readings as a function of joint angle of a prosthesis of FIG. 2 during extension of the prosthesis.

In yet another embodiment, as shown by FIGS. 11 and 12, the sensor 35, 38 measurements are captured by the analysis program 40 and displayed as a pressure graph as a function of joint angle. Specifically, referring to FIGS. 11 and 12, the analysis program 40 displays a two dimensional pressure graph 200, 220 in pounds per square inch (lb/in$^2$) when the prosthesis 30 is moving in the flexion range of motion (FIG. 11) and when the prosthesis 30 is moving in the extension range of motion (FIG. 12). Again, as described in detail above, the pressure distribution graph is representative of the sensed pressure on the spacer 34 by the femoral component 32.

FIG. 11 illustrates a graph plotting the six sensor regions 102 104, 106, 108, 110, 112 marked by their respective reference numerals versus joint angle, wherein the prosthesis 30 is moving in flexion. FIG. 12 illustrates a graph plotting the six sensor regions 102 104, 106, 108, 110, 112 marked by their respective reference numerals versus joint angle, wherein the prosthesis 30 is moving in extension. As the graphs of FIGS. 11 and 12 show, the pressure on each region varies according to joint angle, providing the physician with a graphical understanding of the mechanics of the prosthesis 30 and allowing the physician to adjust their surgical or medical procedures by examining the pressure within the prosthesis 30 over the full range of motion.

It will be understood that the sensor 35, 36, 38 measurements captured by the analysis program 40 and may be displayed in any number of various ways, including, raw data dumps, and as graphs, similar to those disclosed above. For example, in another embodiment (not shown), the analysis program 40 may display a pressure graph as a function of ligament tension. It will be appreciated, however, that the example graphs above are merely illustrative, and are no way limiting.

In still another embodiment, the outputs from the sensors 35, 36, 38 may be transmitted to the main unit 12, wherein they may be captured by another embodiment of the analysis program 40 which may be, for example, a finite element analysis program ("FEA" program). An example of an FEA program is the ANSYS Finite Element Analysis software program marketed by ANSYS Inc. located in Canonsburg, Pa., and commercially available.

Figure 13:
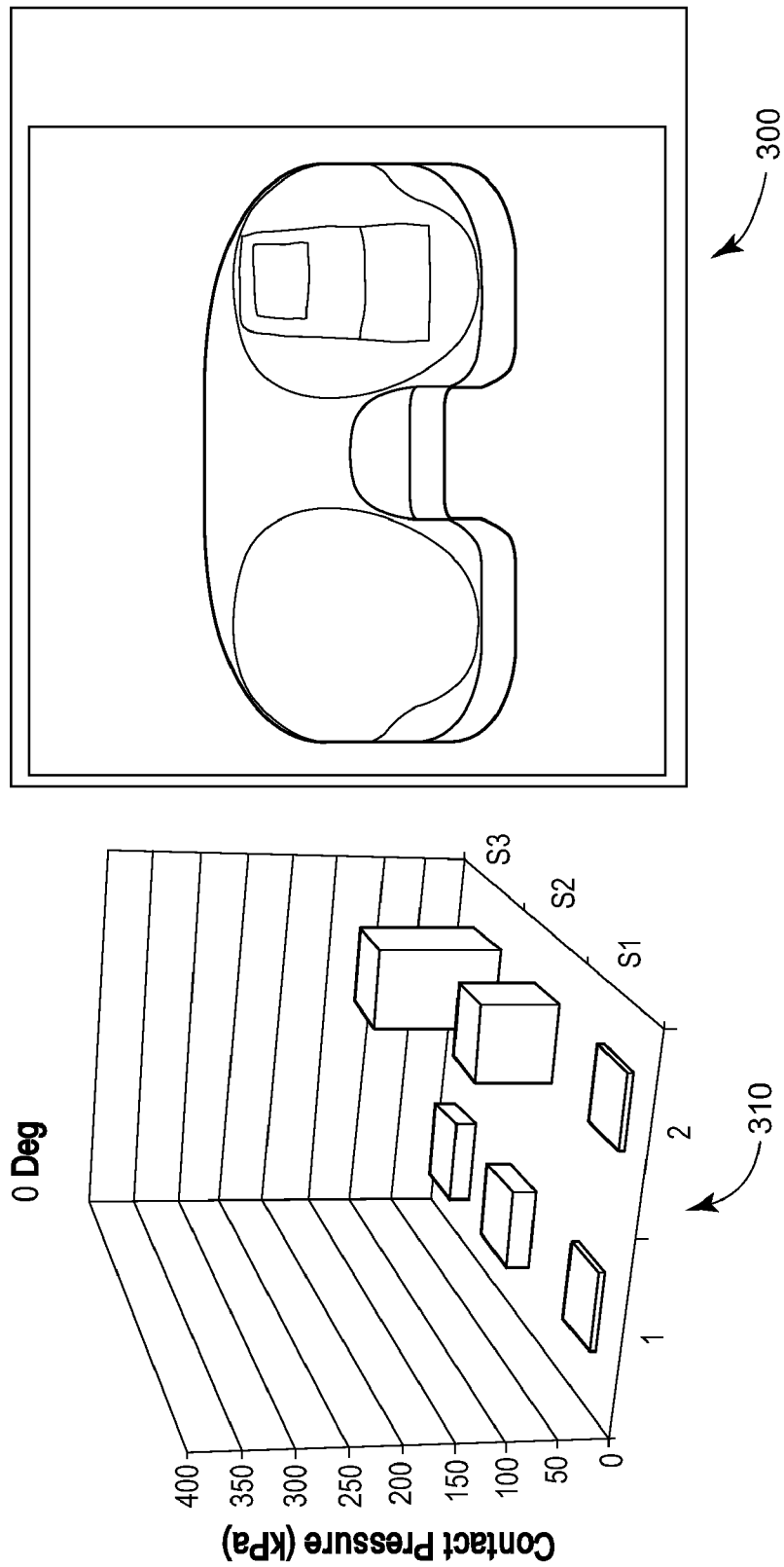
FIG. 13 is a topographical pressure graph plotting pressure readings against a three dimensional rendering of an embodiment of a spacer of FIG. 2.
Figure 14:
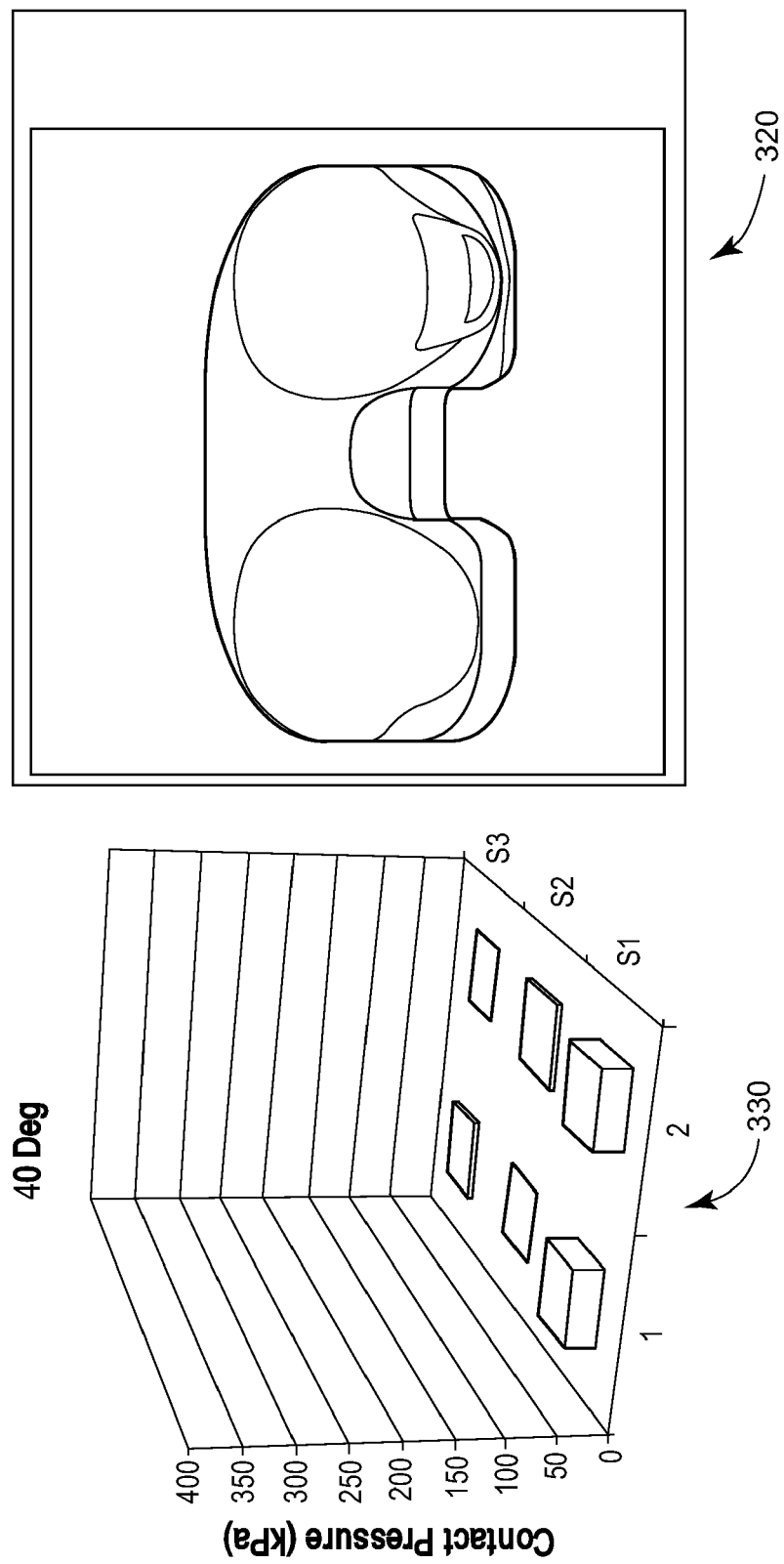
FIG. 14 is a topographical pressure graph plotting pressure readings against a three dimensional rendering of an embodiment of a spacer of FIG. 2.
Figure 15:
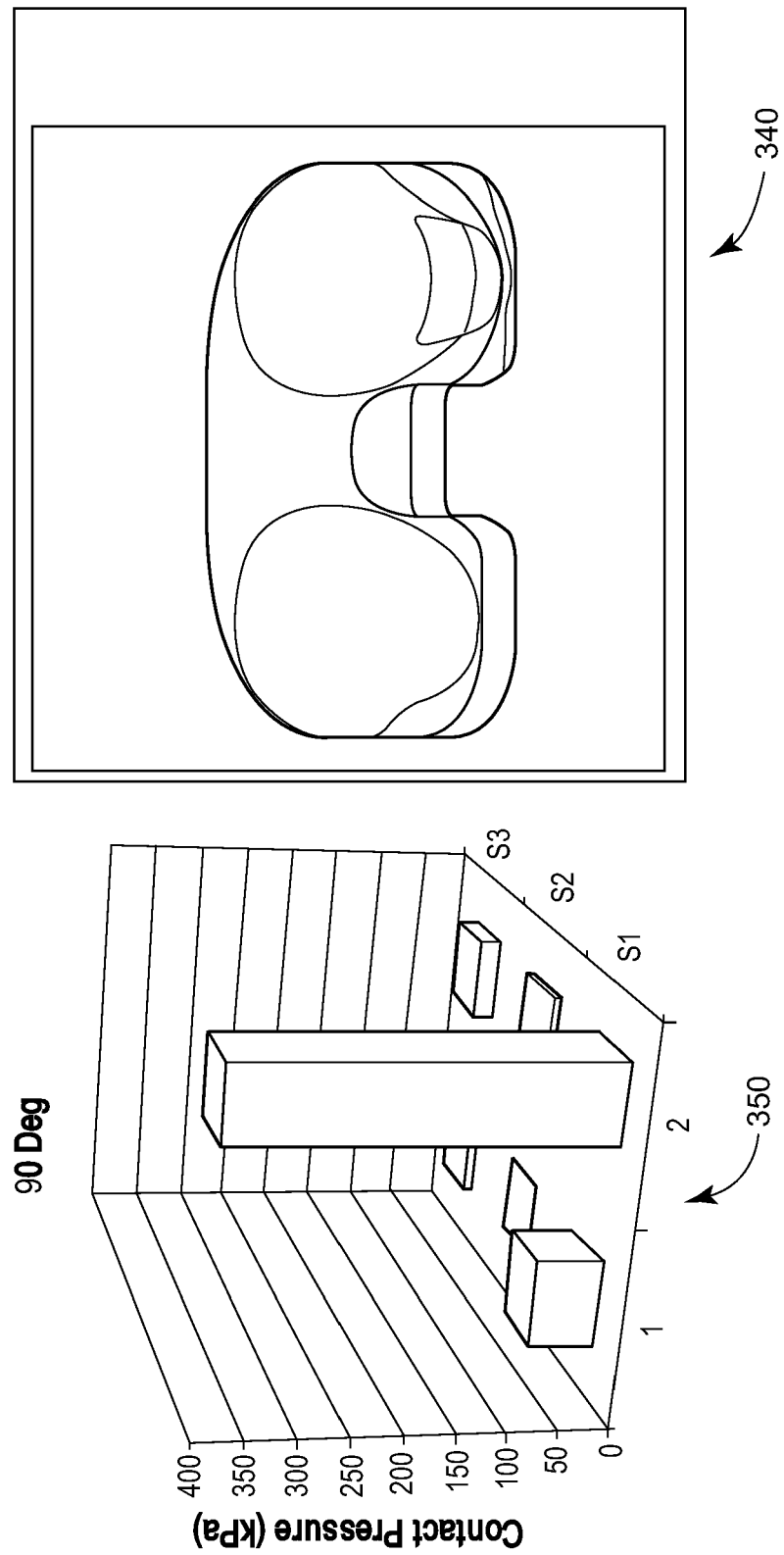
FIG. 15 is a topographical pressure graph plotting pressure readings against a three dimensional rendering of an embodiment of a spacer of FIG. 2.

The FEA analysis program 40 is flexible, and may display the data in a variety of formats on the display(s) 24. In one embodiment, as shown by FIGS. 13 through 15, the sensor 35, 38 measurements are captured by the FEA analysis program 40 and displayed as both a pressure distribution graph, and as a pressure topography graph. Specifically, referring to FIG. 13, the FEA analysis program 40 displays a three dimensional pressure topography graph 300, in kilopascal (kPa) when the prosthesis 30 is in the zero degree (0°) position. Similar to the other embodiments, for example a pressure distribution graph 310, and as described in detail above, the pressure topography graph 300 is representative of the sensed pressure on the spacer 34 by the femoral component 32 at a specific angle. Unlike the pressure distribution graph 310, however, the illustrative pressure topography graph 300 displays the pressure in relationship to the modeled spacer 34, allowing the practitioner to identify the location of the pressure points in spatial relation to the spacer 34 used.

Referring to FIGS. 14 and 15, the analysis program 40 displays a three dimensional pressure topography graph 320, 340 in kilopascal (kPa) when the prosthesis 30 is in the forty degree (40°) position (illustrated by FIG. 14), and when the prosthesis 30 is in the ninety degree (90°) position (illustrated by FIG. 15). As described in above, the illustrative pressure topography graphs 320, 340 displays pressure in relationship to the modeled spacer 34, as opposed to the six region pressure distribution graphs 330, 350.

Figure 16:
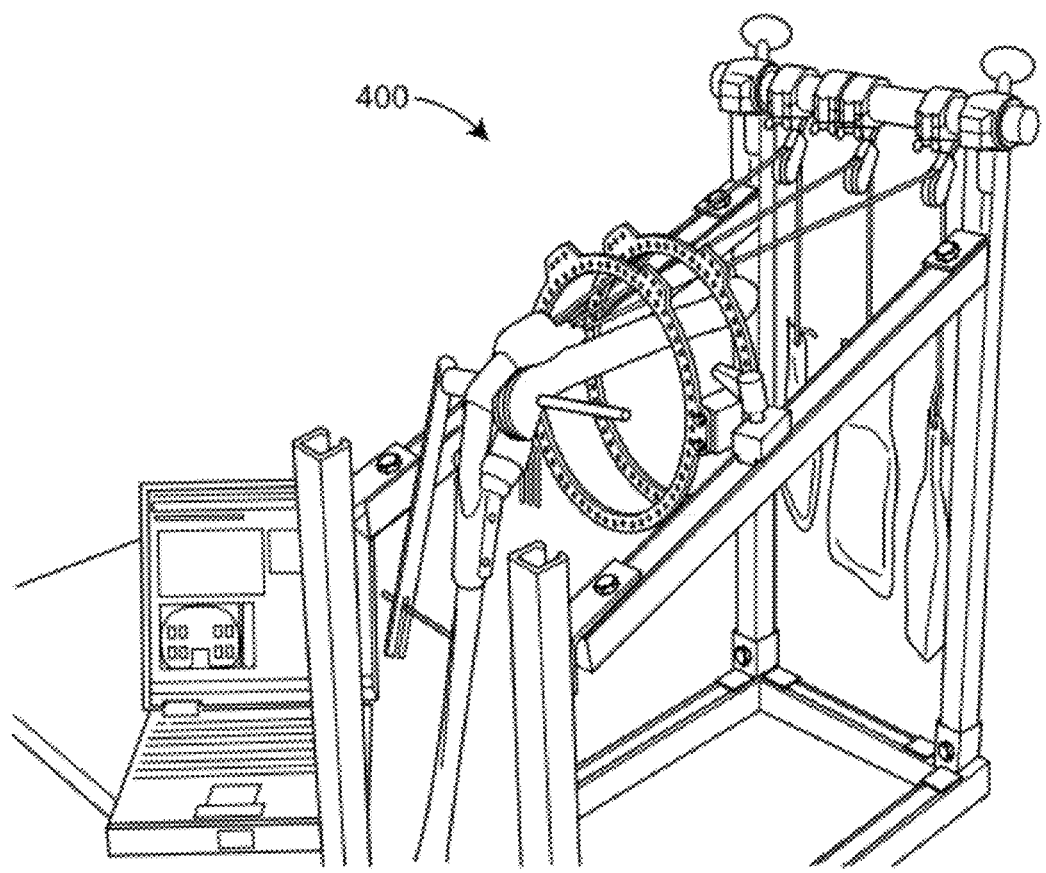
FIG. 16 is a top perspective view of an embodiment of a jig which may be used in conjunction with the system of FIG. 2.

Referring now to FIG. 16, there is illustrated a jig 400 which may be used in the operative environment of FIGS. 6 and 7, or alternatively, in a testing environment, such as cadaver testing, or the like. The jig 400 is arranged to control the flexion of the prosthesis 30 in the intra operative environment is such a way that a number of variables may be controlled. For example, the jig may control, for instance, the rate of flexion and extension, the total range of motion, and the axis of motion, etc., in such a manner that the user may experience consistent and reproducible results when testing various aspects of the prosthesis 30.

It will be noted that while the above description relates to an embodiment of a human a prosthetic, it will be readily understood that the principles of the present invention may be applied to any type of replacement joint, as well as any living organism. For example, the sensors 35 of the present embodiment may be utilized to replace a hip joint, or other joint, including the ankle, foot, shoulder, elbow and fingers. For instance, in hip joint replacement, the damaged ball (the upper end of the femur) is replaced by a metal ball attached to a metal stem fitted into the femur, and a plastic socket is implanted into the pelvis, replacing the damaged socket. The sensors 35 may be embedded within the plastic socket (or other location) to provide the practitioner with data related to the contact between the metal stem and the socket.

Figure 18:
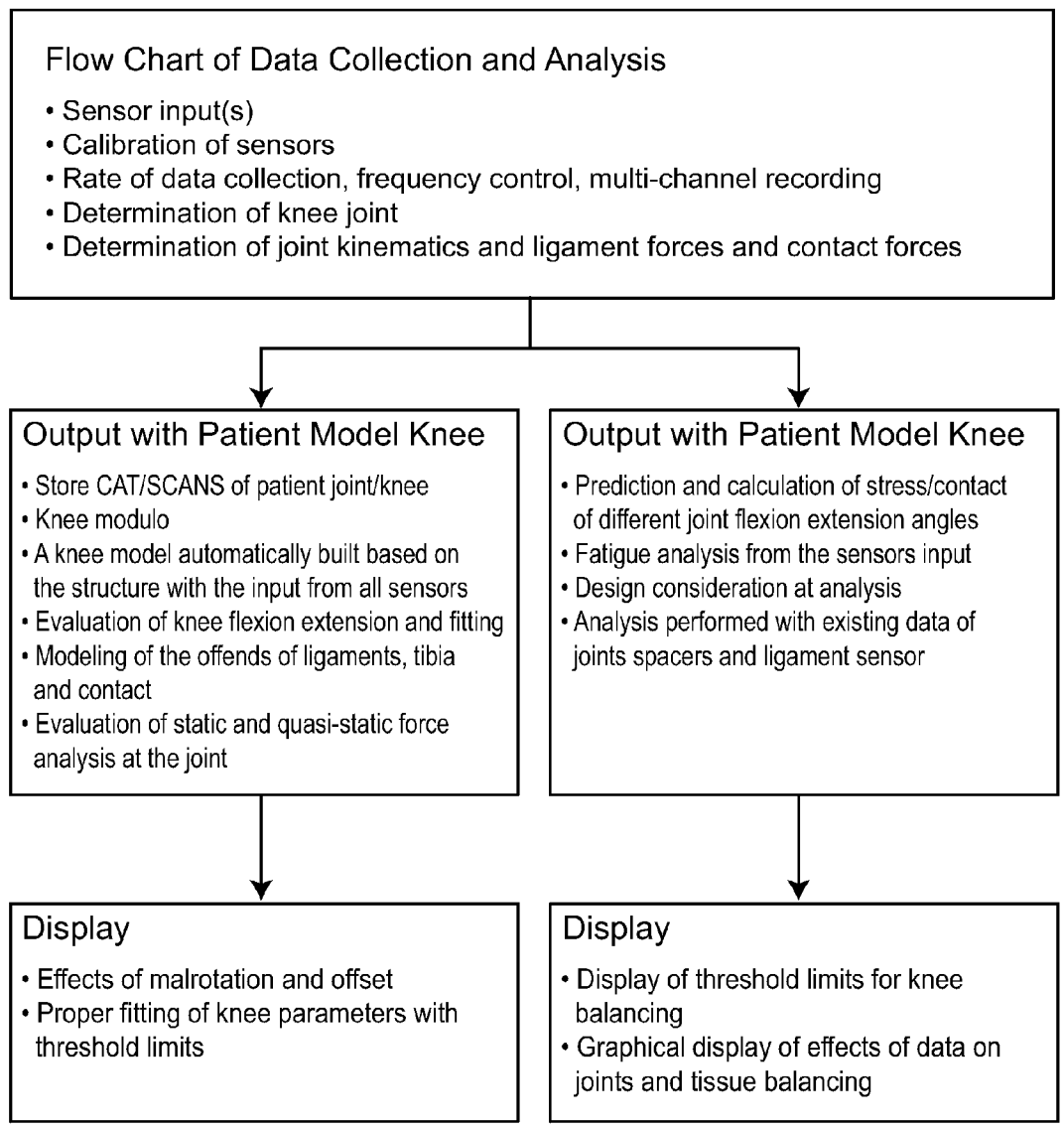
FIG. 18 is a block diagram of an exemplary data collection modeling/analysis display scheme.

It will be further understood that the main unit 12 may be arranged to receive input from an MRI, CAT scan, X-ray, and/or other diagnostic device to feed the analysis program 40 with that input. The analysis program 40 may then convert that input to a model of the patient's knee. The model may reduce or eliminate the need for conventional intermedullar rods conventionally used to determine the specific of the tibial and femoral cut down, such as location, angle, etc. One example of these data collection, finite element analysis and/or joint modeling steps, along with there respective graphical outputs or displays is shown in FIG. 18.

A system and method according to the disclosed example may serve to improve longevity and function of Total Knee Arthroplasty (TKA). The accurate balancing of the forces acting on the joint in a total knee arthroplasty results in proper component placement and proper tensioning of the ligamentous structures that cross the knee joint. When a knee arthroplasty is properly balanced, stresses are evenly distributed in the articulating components through a full range of motion. Functionally poor ligament balance, which can create instability causing acute subluxation or dislocation of the total knee components, may be reduced or eliminated. On the other hand, tight ligaments can produce stiffness limiting or precluding knee motion. More subtle discrepancies in ligament balancing create abnormally high peak stresses in the articular components and at the bone prosthesis interface causing catastrophic failure of polyethylene tibial components or mechanical loosening at the bone cement interface. Additionally, undue stresses can increase component wear, which is deleterious because the wear particles are phagocytized by macrophages initiating an inflammatory cascade that stimulates osteoclast activity. This causes osteolysis with bone loss and degradation of the bone implant interface and eventual loosening.

In accordance with the disclosed example, the necessary experimental and analytical tools to quantify and standardize balancing of the knee joint during TKA may be developed. Additional data may be collected from cadaver total knee arthroplasty experiments in order to correlate stress measurements with abnormalities of ligamentous balance and component position.

Using the system disclosed herein, as the knee is flexed through a complete range of motion the pressures may be collected in real time or in near real time. While the knee is flexed tension will be measured in the structures bridging the joint to measure the effect of increased tension on the stress values. Data may also be obtained on the effect of component malposition on the stresses across the knee.

The data obtained may be used to create a mathematical model for knee arthroplasty. For example, a clinical advisory board of orthopedic surgeons may be established to define possible criteria needed to achieve acceptable conformity in a balanced knee. A rough paradigm may be developed to aid in guiding the surgeon in interpretation of stress data obtained during knee arthroplasty. Stress data may be obtained during total knee implantation intraoperatively using a wireless sensory device. The paradigm may be tested and fine tuned so that stress data can guide the surgeon in achieving proper balance when performing TKA.

The disclosed system may further aid in investigating the force requirements from the collateral segments and how they influence the pressure/contact between the femoral and tibial component during flexion-extension. The effects of pressure on the wear on the polyethylene component of the biomechanics of the knee may be readily studied, threshold limits of pressure values deemed acceptable to balance the knee after TKA may be developed. An analytical dynamical model of the knee will used to analyze the experimental data.

A dynamic model of the knee depicting all the intricate details such as contact in the presence of active forces, patella, collateral ligaments, attachment points, bone density, design characteristic of the prosthesis, interface between bone and femoral-tibial components, may be developed using known methodologies.

In this phase of the study pressure profiles will be created corresponding to specific increments of misalignment. This synthesis will validate the information with the concurrent experiment that has implemented the sensor technology. An advisory board will be set up where clinicians and surgeons will set up threshold for contact pressure in the TKA. Based on precalibrated values of experimental study, the surgeon can then do proper ligament release or component exchange to bring the values within acceptable limits. Eventually, this will be taken as guidelines which will allow a precision fit in the operating room without any reliance on the experience of the surgeon. Effectively this study will lead in achieving a higher level of joint mobility performance in arthritic patient. Ultimately, not only a better tracking mechanism of wear and performance of the TKA will be developed but also the clinician's performance during the surgery will be evaluated through the quantitative feedback he receives.

Based on the results a special jig 400 will be designed to immobilize the femur while allow free motion of the tibia and quadriceps mechanism. The components will then be implanted and the knee will be placed in the special jig 400. A computerized winch will pull on the quadriceps tendon duplicating the force and the direction of the quadriceps muscle. The rectus femoris and vastus intermedius will be tied together and loaded with a 30-N weight, the rectus medialis will be loaded with 25-N weight and the vastus lateralis will be loaded with 20-N. Finally, a high precision potentiometer (shape sensor) will be used to measure the joint angle. The knee will then be flexed and extended from 0 to 9° degrees. A distribution of contact pressure will be recorded as a function of angle. The leg will also be outfitted with an angle sensor on the side of the knee in order to measure joint angle. The sensors will allow readings of stress and tension in real time as the knee is brought through the complete flexion cycle. The effect of each particular reefing on peak joint stresses will be measured and abnormal tension in the shortened ligament will be correlated with peak joint stresses through the flexion cycle. Finally the components will be placed in abnormal positions of valgus, varus, flexion and extension and the pressures again measured through the flexion cycle.

A Sample Experimental Procedure:

An experimental knee replacement procedure was performed on a mock human knee 50. Once the experimental knee replacement surgery was performed, a traditional spacer was removed and replaced with one that had six pressure sensors 35. the sensors 35 and the main unit 12 were coupled through the use of wires. The knee 50 was stitched with the wires running through the wound. The femur 52 was immobilized with the jig 400 and the quadriceps were loaded. The joint angle sensors 36 were put in place. The knee 50 was then extended and flexed through the normal range of motion many times. The rate pf flexion was approximately 20 degrees per second. Caution was taken in order not to apply external varus or valgus stress. The cycle of extension and flexion was repeated many times and recordings were averaged.

A finite element model was created by scanning the actual spacer 34 with a laser micrometer and importing the geometry into a computer file. Using Autocad, a three dimensional file was refined and then exported to an ANSYS compatible format. The current ANSYS spacer model has over 23,000 elements, which have 20 nodes each and a tetrahedral shape. On the surface of each condyle 66, 68, twelve hundred and fifty nine (1259) nodes resided. These nodes are responsible for the application of all pressure and forces to the model while the bottom surface is constrained to have zero displacement. The spacer model was designed so that data could be inputted into the model easily using data from the output sensors 35. ANSYS was then used to generate the necessary plots of stress—both principal stresses and von-Mises stress plots of the deformation of the tibia component were be displayed as function of time variant pressure do to tibiofemoral contact.

The contact pressures at each sensor 35 was displayed for knee extension and flexion. The joint angle range of motion varied from roughly ninety degree (90°) to zero degrees (0°). During knee extension, very small contact forces were recorded while the knee was between ninety degrees (90°) and fifty degrees (50°). For example, one sensor showed activity between fifty degrees (50°) and tweenty five degrees (25°) with a maximum of 40 psi at approximately 35°. Another sensor recorded a maximum at sixteen degrees (16°) with pressure of 110 psi. During flexion, contact pressures were recorded with slightly larger magnitudes. For example one sensor, which recorded no more than 3-psi during extension, recorded 10-psi at around seventy five degrees (75°) during flexion. Similarly, another sensor which recorded a maximum at thirty five degrees (35°) during extension, recorded a maximum while at twenty five degrees (25°) during flexion.

As a result, it may be concluded that for this experiment, forces on the medial and lateral condyle were not balanced in phase or magnitude. This would suggest a varus-valgus unstable knee. The high pressure recorded at the extended end of the graph suggested a joint that is too tight.

Numerous modifications and alternative embodiments of the invention will be apparent to those skilled in the art in view of the forgoing description. Accordingly, this description is to be construed as illustrative only and is for the purpose of teaching those skilled in the art the best mode of carrying out the invention. The details of the system may be varied substantially without departing from the spirit of the invention, and the exclusive use of all modifications which are within the scope of any subsequent claims is reserved.

What is claimed is:

1. A system for prosthesis fitting in joints comprising:
   an artificial condyle;
   a spacer, the spacer cooperating with the condyle to form an artificial joint, the spacer adapted to support a force from the condyle, the artificial joint being adapted to move between a flexed position and an extended position defining a range of motion;
   a sensor embedded within the spacer, the sensor being responsive to the force, wherein the sensor generates an output representative of the force;
   a processor having a memory, the processor being operatively coupled to the sensor, the processor memory being adapted to store the output representative of the force on the spacer by the condyle;
   a computer analysis program stored on the processor memory, the computer analysis program being adapted to analyze the output representative of the force on the spacer,
   wherein the computer analysis program is a finite element analysis program.

2. A system for prosthesis fitting in joints as defined in claim 1, wherein the artificial joint is moveable through a range of motion, and wherein the sensor is arranged to provide a plurality of outputs each corresponding to a plurality of angles of the artificial joint within the range of motion.

3. A system for prosthesis fitting in joints as defined in claim 1, wherein the sensor is a strain gage, the strain gage being adapted to generate a voltage in response to the forces on the spacer.

4. A system for prosthesis fitting in joints as defined in claim 1, wherein the sensor comprises an array of individual sensors embedded in the spacer.

5. A system for prosthesis fitting in joints as defined in claim 4, wherein each of the individual sensors is embedded within a recess formed in the spacer.

6. A system for prosthesis fitting in joints as defined in claim 1, wherein the spacer comprises a transceiver having a memory, the transceiver being operatively coupled to the sensor.

7. A system for prosthesis fitting in joints as defined in claim 6, wherein the transceiver is arranged to wirelessly communicate with the processor.

8. A system for prosthesis fitting in joints as defined in claim 1, further comprising a database, wherein the database is adapted to store the output representative of the force on the spacer.

9. A system for prosthesis fitting in joints as defined in claim 1, wherein the finite element analysis program is adapted to output a pressure topography graph.

10. A system for prosthesis fitting in joints as defined in claim 9, further comprising a display, wherein finite element analysis program is adapted to output the pressure topography graph on display.

11. A system for prosthesis fitting in joints as defined in claim 1, further comprising a ligament tension sensor, the tension sensor adapted for placement on a ligament and arranged to produce an output indicative of a tensile force applied to the ligament.

12. A system for prosthesis fitting in joints as defined in claim 11, further comprising a display, wherein the data representative of the force is illustrated as a function of the tensile force applied to the ligament.

13. A system for prosthesis fitting in joints as defined in claim 2, further comprising a joint angle sensor, the joint angle sensor being responsive to the range of motion of the artificial joint, wherein the sensor generates data representative of an angle of the artificial joint.

14. A system for prosthesis fitting in joints as defined in claim 12, further comprising a display, wherein the data representative of the force is illustrated as a function of the joint angle.

15. A system for prosthesis fitting in joints as defined in claim 2, including a jig arranged to move the artificial joint through the range of motion.

16. A system for prosthesis fitting in joints as defined in claim 14, wherein the jig is arranged to move the artificial joint at a controlled rate of flexion.

17. A system for prosthesis fitting in joints as defined in claim 14, wherein the jig includes an angle sensor.

18. A system for prosthesis fitting in joints as defined in claim 14, wherein the jig is arranged to control at least one of a varus angle and a valgus angle.

19. A system for prosthesis fitting in joints as defined in claim 14, wherein the jig is arranged to apply a controlled load to the artificial joint.

20. A system for prosthesis fitting in joints as defined in claim 1, further comprising:
  a ligament tension sensor, the tension sensor being responsive to the range of motion of the artificial joint, wherein the sensor generates data representative of tension on a ligament of the joint;
  a joint angle sensor, the joint angle sensor being responsive to the range of motion of the artificial joint, wherein the sensor generates data representative of an angle of the artificial joint; and
  wherein the data representative of the force is illustrated as a function of the joint angle and as a function of the ligament tension.

21. A system for prosthesis fitting in joint arthroplasty comprising:
  an artificial condyle;
  a spacer, the spacer cooperating with the condyle to form an artificial joint, the spacer adapted to support a force from the condyle, the artificial joint being adapted to move between a flexed position and an extended position defining a range of motion;
  a sensor embedded within the spacer, the sensor being responsive to the force, wherein the sensor generates an output representative of the force;
  a ligament tension sensor, the tension sensor being responsive to the range of motion of the artificial joint, wherein the sensor generates data representative of tension on a ligament of the artificial joint;
  a joint angle sensor, the joint angle sensor being responsive to the range of motion of the artificial joint, wherein the sensor generates data representative of an angle of the artificial joint;
  a processor having a memory, the processor being operatively coupled to the sensor, the processor memory being adapted to store the output representative of the force on the spacer by the condyle;
  a computer analysis program stored on the processor memory, the computer analysis program being adapted to intraoperatively analyze the output representative of the force on the spacer, the data representative of an angle of the artificial joint, and the data representative of tension on a ligament of the artificial joint,
  wherein the computer analysis program is a finite element analysis program.

22. A system of claim 21, wherein the artificial joint is moveable through a range of motion, and wherein the sensor is arranged to provide a plurality of outputs each corresponding to a plurality of angles of the artificial joint within the range of motion.

23. A system of claim 22, wherein each of the individual sensors is embedded within a recess formed in the spacer.

24. A system of claim 21, wherein the spacer comprises a transceiver having a memory, the transceiver being operatively coupled to the sensor and wherein the transceiver is arranged to wirelessly communicate with the processor.

25. A system of claim 21, further comprising a database, wherein the database is adapted to store the output representative of the force on the spacer, the data representative of an angle of the artificial joint, and the data representative of tension on a ligament of the artificial joint.

26. A system of claim 21, wherein the computer analysis program is a finite element analysis program.

27. A system of claim 26, wherein the finite element analysis program is adapted to output a pressure topography graph and wherein the computer analysis program is adapted to receive and output load threshold limits to the pressure topography graph.

28. A method for prosthesis fitting in joints comprising:
  creating a finite element model of a knee joint in a computer;
  providing an artificial condyle;
  providing a spacer, the spacer cooperating with the condyle to form an artificial joint, the spacer adapted to support a force from the condyle, the artificial joint being adapted to move between a flexed position and an extended position defining a range of motion;
  embedding a sensor within the spacer, the sensor being responsive to the force, wherein the sensor generates an output representative of the force; storing the output representative of the force on the spacer by the condyle in a processor having a memory, the processor being operatively coupled to the sensor;
  importing the output representative of the force into the finite element model; and
  analyzing the output representative of the force on the spacer in a computer finite element analysis program stored on the processor memory.

29. A method for prosthesis fitting in joints as defined in claim 28, wherein the artificial joint is moveable through a range of motion, and further comprising arranging the sensor to provide a plurality of outputs each corresponding to a plurality of angles of the artificial joint within the range of motion.

30. A method for prosthesis fitting in joints as defined in claim 28, further comprising arranging the sensor as an array of individual sensors embedded in the spacer.

31. A method for prosthesis fitting in joints as defined in claim 30, further comprising embedding each of the individual sensors within a recess formed in the spacer.

32. A method for prosthesis fitting in joints as defined in claim 28, further comprising transmitting the output representative of the force via a transceiver having a memory, the transceiver being operatively coupled to the sensor.

33. A method for prosthesis fitting in joints as defined in claim 32, further comprising embedding the transceiver within the spacer.

34. A method for prosthesis fitting in joints as defined in claim 32, further comprising transmitting the output representative of the force by wirelessly communicating with the processor.

35. A method for prosthesis fitting in joints as defined in claim 28, further comprising storing the output representative of the force on the spacer in a database.

36. A method for prosthesis fitting in joints as defined in claim 28, further comprising displaying the analysis of the output representative of the force on the spacer on a display.

37. A method for prosthesis fitting in joints as defined in claim 36, further comprising displaying a pressure topography graph.

38. A method for prosthesis fitting in joints as defined in claim 29, further comprising providing a ligament tension sensor, the tension sensor adapted for placement on a ligament and arranged to produce an output indicative of a tensile force applied to the ligament.

39. A method for prosthesis fitting in joints as defined in claim 38, further comprising displaying the data representative of the force as a function of the tensile force applied to the ligament.

40. A method for prosthesis fitting in joints as defined in claim 29, further comprising providing a joint angle sensor, the joint angle sensor being responsive to the range of motion of the artificial joint to generate data representative of an angle of the artificial joint.

41. A method for prosthesis fitting in joints as defined in claim 40, further comprising displaying the data representative of the force as a function of the joint angle.

42. A method for prosthesis fitting in joints as defined in claim 29, further comprising moving the artificial joint through the range of motion.

43. A method for prosthesis fitting in joints as defined in claim 42, further comprising controlling the range of motion of the artificial joint with a jig.

44. A method for prosthesis fitting in joints as defined in claim 42, further comprising controlling the rate of flexion of the artificial joint with a jig.

45. A method for prosthesis fitting in joints as defined in claim 42, further comprising controlling the rate of extension of the artificial joint with a jig.

46. A method for prosthesis fitting in joints as defined in claim 42, further comprising controlling at least one of a vargus angle and a valgus angle of the artificial joint with a jig.

47. A method for prosthesis fitting in joints as defined in claim 42, further comprising controlling a load to the artificial joint with a jig.

\* \* \* \* \*